US010156782B2

(12) United States Patent
Huber

(10) Patent No.: US 10,156,782 B2
(45) Date of Patent: Dec. 18, 2018

(54) MASK FOR EUV LITHOGRAPHY, EUV LITHOGRAPHY APPARATUS AND METHOD FOR DETERMINING A CONTRAST PROPORTION CAUSED BY DUV RADIATION

(71) Applicant: Carl Zeiss SMT GmbH, Oberkochen (DE)

(72) Inventor: Peter Huber, Heidenheim (DE)

(73) Assignee: CARL ZEISS SMT GMBH, Oberkochen (DE)

( * ) Notice: Subject to any disclaimer, the term of this patent is extended or adjusted under 35 U.S.C. 154(b) by 157 days.

(21) Appl. No.: 15/431,306

(22) Filed: Feb. 13, 2017

(65) Prior Publication Data

US 2017/0219920 A1 Aug. 3, 2017

Related U.S. Application Data

(63) Continuation of application No. PCT/EP2015/067142, filed on Jul. 27, 2015.

(30) Foreign Application Priority Data

Aug. 13, 2014 (DE) ........................ 10 2014 216 121

(51) Int. Cl.
| | |
|---|---|
| G03F 1/24 | (2012.01) |
| G03F 1/44 | (2012.01) |
| G03F 1/46 | (2012.01) |
| G03F 1/54 | (2012.01) |
| G03F 1/58 | (2012.01) |
| G03F 1/60 | (2012.01) |
| G03F 7/20 | (2006.01) |
| G01N 21/33 | (2006.01) |

(52) U.S. Cl.
CPC ............. *G03F 1/24* (2013.01); *G01N 21/33* (2013.01); *G03F 1/44* (2013.01); *G03F 1/46* (2013.01); *G03F 1/54* (2013.01); *G03F 1/58* (2013.01); *G03F 1/60* (2013.01); *G03F 7/70058* (2013.01); *G03F 7/70591* (2013.01); *G03F 7/70616* (2013.01); *G03F 7/70941* (2013.01)

(58) Field of Classification Search
CPC ..... G03F 1/24; G03F 1/44; G03F 1/46; G03F 1/54; G03F 1/58; G03F 1/60; G03F 7/70058; G03F 7/70591; G03F 7/70616; G03F 7/70941; G01N 21/33
USPC ...................................................... 430/5, 30
See application file for complete search history.

(56) References Cited

U.S. PATENT DOCUMENTS

| | | |
|---|---|---|
| 6,593,037 B1 | 7/2003 | Gabriel et al. |
| 7,838,177 B2 | 11/2010 | Kanayama et al. |
| 2002/0142620 A1 | 10/2002 | Yan et al. |
| 2004/0131948 A1 | 7/2004 | Yan et al. |
| 2005/0221238 A1 | 10/2005 | Dierichs |
| 2013/0196255 A1 | 8/2013 | Hayashi et al. |
| 2015/0072271 A1 | 3/2015 | Lu et al. |

FOREIGN PATENT DOCUMENTS

EP 1833080 A1 9/2007

OTHER PUBLICATIONS

International Search Report and Written Opinion in counterpart International Application No. PCT/EP2015/067142, dated Dec. 9, 2015, 29 pages.
Davydova et al., "Best Poster-EMLC14 Black Border, Mask 3D Effects: Covering Challenges of EUV Mask Architecture for 22 NM Node and Beyond", Bacus News, vol. 30, No. 9, 2014.
Lorusso et al., "Metrology Development for Extreme Ultraviolet Lithography: Flare and Out-Of-Band Qualification", Journal of Vacuum Science and Technology: Part B., vol. 29, No. 6, Nov. 2011.
Lorusso et al., "Deep Ultraviolet Out-of-Hand Characterization of EUVL Scanners and Resists", Proceedings of SPIE, vol. 8679, Apr. 2013, p. 1-3.
Yu et al., "An Accurate Method to Determine the Amount of Out-of-Band Light in an EUV Scanner", Proceedings of SPIE, vol. 9422, Mar. 2015.
George et al., "Asserting Out-of-Band Flare Effects at the Wafer Level for EUV Lithography", Proceedings of SPIE, vol. 7636, Mar. 2010.
Office Action in corresponding German Application 10 2014 216 121.5, dated Feb. 9, 2015, along with English Translation.
International Search Report and Written Opinion in counterpart International Application No. PCT/EP2015/067142, dated Dec. 9, 2015, 19 pages.

*Primary Examiner* — Christopher G Young
(74) *Attorney, Agent, or Firm* — Edell, Shapiro & Finnan, LLC

(57) ABSTRACT

A mask (M) for EUV lithography includes: a substrate (7), a first surface region ($A_1$) formed by a surface (8a) of a multilayer coating (8) embodied to reflect EUV radiation (27), said surface (8a) facing away from the substrate (7), and a second surface region ($A_2$) formed by a surface (18a) of a further coating (18) embodied to reflect DUV radiation (28) and to suppress the reflection of EUV radiation (27), said surface (18a) facing away from the substrate (7). The further coating is a multilayer coating (18). Also disclosed are an EUV lithography apparatus that includes such a mask (M) and a method for determining a contrast proportion caused by DUV radiation when imaging a mask (M) onto a light-sensitive layer.

16 Claims, 4 Drawing Sheets

MASK FOR EUV LITHOGRAPHY, EUV LITHOGRAPHY APPARATUS AND METHOD FOR DETERMINING A CONTRAST PROPORTION CAUSED BY DUV RADIATION

CROSS REFERENCE TO RELATED APPLICATION

This is a Continuation of International Application PCT/EP2015/067142, which has an international filing date of Jul. 27, 2015, and the disclosure of which is incorporated in its entirety into the present Continuation by reference. The following disclosure is also based on and claims the benefit of and priority under 35 U.S.C. § 119(a) to German Patent Application No. DE 10 2014 216 121.5, filed Aug. 13, 2014, which is also incorporated in its entirety into the present Continuation by reference.

FIELD OF THE INVENTION

The invention relates to a mask for EUV lithography and a method for determining a contrast proportion caused by DUV radiation when imaging the mask, or a mask, onto a light-sensitive layer.

BACKGROUND

Microlithographic projection exposure apparatuses serve to produce microstructured components using a photolithographic method. In so doing, a structure-bearing mask, the so-called reticle, is imaged onto a light-sensitive layer with the aid of a projection system. A shorter wavelength of the employed imaging light allows smaller structures to be imaged onto the mask with the aid of the projection system. In so-called EUV lithography apparatuses, use is made of imaging light with a used wavelength in the extreme ultraviolet (EUV) range between approximately 5 nm and approximately 20 nm. In the case of such a used wavelength in the range between 5 nm and 20 nm, use is only made of reflective optical elements (EUV mirrors) for imaging purposes and the structure-bearing mask is also a reflecting optical element, onto which a structured absorbing layer or coating has been applied in order to generate the desired structures when imaging on the light-sensitive layer.

An EUV lithography apparatus comprises a light source for generating EUV radiation for illuminating the reticle or the mask. In addition to the desired used wavelength in the EUV wavelength range (for example at approximately 13.5 nm), currently known light sources for generating EUV radiation also emit radiation at many other wavelengths. While EUV radiation is already significantly attenuated by the reflection at a plurality of EUV mirrors placed in the beam path in succession, radiation in the DUV, UV, VIS and IR wavelength ranges may be reflected, in part without impediment, at all EUV mirrors and at the mask and may reach the light-sensitive layer or the wafer. The latter is problematic, in particular for the DUV proportion of the radiation emitted by the EUV light source, since the light-sensitive layer, i.e. the photoresist (also referred to as resist), which is applied onto the wafer, is exposed not only by the EUV radiation proportion but also by the DUV radiation proportion, with the exposure by the latter proportions being very blurred and not defined, i.e. the DUV radiation proportion does not generate precise imaging or does not generate a precise image of the structures on the mask on the wafer.

Solutions for removing DUV radiation before it may reach the light-sensitive layer are known, but, in practice, these solutions are almost always connected with a significant light loss in the EUV wavelength range. It is therefore desirable to be able to use EUV lithography apparatuses without DUV suppression or with only a weak DUV suppression.

It is essential for the use of such EUV lithography apparatuses to precisely know what proportion of the contrast on the light-sensitive layer or on the wafer is caused by the DUV radiation proportion in the radiation emitted by the EUV light source. This contrast proportion may not be too large because, otherwise, imaging of the structures formed on the mask is carried out with an insufficient contrast. The DUV radiation proportion depends strongly on the respective settings of the EUV light source or of the illumination system; the contrast at the respective wavelength depends, inter alia, on the employed resist.

U.S. Pat. No. 6,593,037 B1 discloses a reflective mask (reticle) for EUV lithography, said mask being embodied to reduce reflections at an absorbing coating at wavelengths shorter than in the DUV wavelength range. The reflective mask is embodied to generate additional reflections which have a desired phase difference in respect of the reflections at the absorbing coating such that the additional reflections reduce or eliminate the reflections at the absorbing coating by way of destructive interference. The absorbing coating may have two or more layers, the layer thicknesses and layer number of which being selected in such a way that reflections at a specific EUV wavelength are minimized. The absorbing coating is typically applied to a buffer layer which is arranged above a multilayer coating for reflecting EUV radiation.

SUMMARY

It is an object of the invention to specify a mask for EUV lithography and a method, with which it is possible to determine a contrast proportion caused by DUV radiation when imaging the mask, or a mask, onto a light-sensitive layer.

In accordance with a first aspect, this object is achieved by a mask for EUV lithography, comprising: a substrate, a first (typically contiguous) exposed surface region which is formed by a surface of a multilayer coating embodied to reflect EUV radiation, said surface facing away from the substrate, and a second (typically contiguous) exposed surface region which differs from the first surface region, said second surface region being formed by a surface of a further coating embodied to reflect DUV radiation and suppress the reflection of EUV radiation, said surface of the further coating facing away from the substrate.

In accordance with this aspect of the invention, the use of a special mask is proposed in order to determine the contrast proportion which is caused by a radiation proportion in the DUV wavelength range, i.e. between approximately 100 nm and approximately 400 nm, preferably between approximately 140 nm and approximately 400 nm, in particular between approximately 140 nm and approximately 300 nm, when imaging the mask on the light-sensitive layer.

Like in the case of a conventional EUV mask, a multilayer coating is applied onto a surface of the substrate in the case of such a mask, said multilayer coating being embodied to reflect EUV radiation but a proportion of DUV radiation also being reflected thereon. Additionally, a further coating is applied to the substrate, said further coating being embodied to reflect DUV radiation and to suppress the reflection of EUV radiation. By way of example, the further coating may be an individual metallic layer, in particular a layer made of aluminum, which reflects virtually 100% of DUV radiation and virtually 0% of EUV radiation.

The mask described further above may be used to measure, to a good approximation, the DUV contrast proportion, i.e. the contrast proportion which is caused by the DUV radiation in the light-sensitive layer, independently of the EUV contrast proportion, i.e. the contrast proportion which is generated by the EUV radiation when imaging the mask. For such a measurement, a plurality of exposures during which the mask is imaged onto the light-sensitive layer are carried out for a predetermined combination of parameters of the EUV light source or of the illumination system and a predetermined type of light-sensitive layer (resist).

Here, radiation which is reflected by the surface region of the mask, at which the reflecting multilayer coating is exposed, is imaged onto a first region of the light-sensitive layer while radiation which is reflected by the second surface region of the mask, at which the further coating is applied, is imaged onto a second region of the light-sensitive layer which differs from the first.

For the purposes of determining the contrast or the contrast ratio, a plurality of exposures of light-sensitive layers with an identical resist and a different, typically increasing exposure duration are typically carried out in order to determine the dose required for exposing through the resist in the respective region (the so-called "dose to clear"). The dose required for exposing the second region, at which the radiation reflected by the further coating is incident, represents a measure for the DUV contrast, while the dose required for exposing the first region, at which the radiation reflected by the multilayer coating is incident, represents a measure for the DUV+EUV contrast as both EUV radiation and DUV radiation are reflected at the multilayer coating.

The following relationship approximately applies to the relationship between the DUV contrast and the DUV+EUV contrast and the respective dose to clear:

DUV contrast/DUV+EUV contrast=Dose to clear (multilayer coating)/Dose to clear (further coating)

In the manner described above, it is possible to approximately determine the DUV contrast proportion relative to the overall contrast.

Preferably, the mask comprises a third exposed surface region, which differs from the first and second surface regions, said third surface region being formed by a surface of a coating which absorbs EUV radiation, said surface facing away from the substrate. In contrast to a conventional EUV mask, both the absorbing coating and the multilayer coating are typically not structured. However, as a rule, the layer materials of the multilayer coating and of the absorbing coating correspond to those of a conventional mask for EUV lithography.

Determining the DUV contrast proportion in accordance with the formula above is correct if the reflection behavior of the third surface region with the absorbing coating in the DUV wavelength range has a low reflectivity.

Both the further coating and the multilayer coating may be applied to a portion of the absorbing coating in each case, said absorbing coating itself in this case typically being applied to the substrate over the whole area thereof. Alternatively, the multilayer coating may be applied to the substrate over the whole area thereof and the absorbing coating may be applied to a portion of the multilayer coating, with the further coating being applied in a portion of the absorbing coating. By only applying the further coating and the multilayer coating in a portion, a surface region of the absorbing coating is exposed, said surface region being imaged onto a third region of the light-sensitive layer.

This is advantageous since the absorbing coating absorbs EUV radiation but, as a rule, also reflects radiation in the DUV wavelength range. Since a conventional mask has both portions at which the incident radiation impinges on the surface of the multilayer coating and portions at which the incident radiation impinges on the structured absorbing coating, the DUV contrast proportion of a conventional mask in the case of such an absorbing coating also depends on which proportion of the DUV radiation is reflected at the absorbing coating. By determining the dose required for exposing the third region of the light-sensitive layer, it is also possible to take account of the DUV contrast proportion at the light-sensitive layer which is caused by the absorbing coating.

In a further embodiment the further coating is a multilayer coating. Typically, it is not possible to clean a metallic layer, e.g. made of aluminum, with standard cleaning processes for coated masks, e.g. by treatment with activated hydrogen or oxygen since there may possibly be aging or a change in the optical properties of the A1 layer in this case. If the further coating is embodied as a multilayer coating, it typically may be cleaned using a conventional cleaning process, in particular if the further multilayer coating has identical or similar layer materials to the multilayer coating embodied to reflect EUV radiation.

A further problem in the use of a metallic layer, specifically an aluminum layer, consists of the fact that the spectral reflectivity of the aluminum layer, in particular in the DUV wavelength range, is not identical to the spectral reflectivity of the multilayer coating reflecting EUV radiation. In order to precisely determine the sought-after DUV contrast, the exact spectrum or the spectral distribution of the EUV light source, the spectrum of all layers of the multilayer coating and the wavelength-dependent spectrum of the sensitivity of the resist or of the light-sensitive layer really are required. However, these variables are typically not known, only known approximately or only known for specific wavelengths.

In an advantageous development, the wavelength-dependent reflectivity of the further multilayer coating for DUV radiation in the wavelength range between 140 nm and 400 nm, preferably in the wavelength range between 140 nm and 300 nm, does not deviate by more than +/−5%, preferably by no more than +/−1%, from the wavelength-dependent reflectivity of the multilayer coating in this wavelength range.

Ideally, the wavelength-dependent reflectivity of the further multilayer coating in the aforementioned wavelength range corresponds to the wavelength-dependent reflectivity of the multilayer coating. This may be achieved by virtue of the layer thicknesses, the layer materials and the layer number of the further multilayer coating being selected or optimized in a suitable manner such that the reflectivity of the further multilayer coating at each wavelength within the wavelength range specified above does not deviate by more than approximately +/−5% from the reflectivity of the multilayer coating. Therefore, the reflectivity of the further multilayer coating is distributed about the wavelength-dependent reflectivity of the reflecting coating within an "error band" of +/−5%, preferably +/−1%. In particular, the further multilayer coating may have an aperiodic layer design to this end.

In particular, if the wavelength-dependent reflectivity of the further multilayer coating in the aforementioned wavelength range corresponds to the wavelength-dependent reflectivity of the multilayer coating, the contrast proportion caused by the DUV radiation may also be determined particularly easily for the case where the reflectivity of the absorbing coating in the DUV wavelength range is low.

To this end, the radiation dose/dose to clear $D_3$, which is required for exposing a third region on the light-sensitive substrate and which is reflected by the coating absorbing EUV radiation, is determined first. On the basis of this radiation dose, and the corresponding radiation doses $D_1$ and $D_2$ of the radiation reflected at the multilayer coating and the further coating, it is possible to determine the contrast proportion $K_{DUV}/K_{DUV+EUV}$ caused by the DUV radiation in accordance with the following equation:

$$K_{DUV}/K_{DUV+EUV}=(A_3/D_3+(A_1+A_2)/D_2)/(A_3/D_3+(A_1+A_2)/D_1).$$

Here, $A_1$, $A_2$ and $A_3$ denote the surface regions formed on the mask by the surfaces of the multilayer coating, the further coating and the coating which absorbs EUV radiation. It is understood that the sum of the three surface regions $A_1+A_2+A_3$ in the formula above may be normalized to one such that the three surface regions $A_1$, $A_2$ and $A_3$ may be specified in, for example, %. If $A_3=0$ or $D3 \to \infty$ applies to the third surface region (since hardly any DUV light is reflected), the simplified formula for the contrast proportion of the DUV radiation specified further above emerges.

In an advantageous embodiment, the reflectivity of the further coating, in particular of the multilayer coating, is less than 0.3%, preferably less than 0.1%, at a used wavelength of the EUV radiation, at which the reflectivity of the multilayer coating is at a maximum. A reflectivity of the further coating which is as low as possible for EUV radiation at the used wavelength is advantageous in order to be able to determine the proportion of the DUV contrast as accurately as possible. The reflectivity of the further (multilayer) coating may satisfy the condition specified above, in particular in a wavelength range, which, for example, may lie at +/−0.25 nm or +/−0.5 nm, around the used wavelength. The layer thicknesses and the layer materials of the further multilayer coating may be optimized, for example by numerical calculations, in such a way that, firstly, the reflectivity of the multilayer coating in the DUV wavelength range is reproduced as exactly as possible and, secondly, the reflectivity for radiation in the EUV wavelength range is minimized.

In a further embodiment, the multilayer coating comprises a multiplicity of alternating layers made of a layer material with a high refractive index and a layer material with a low refractive index. For the purposes of reflecting the EUV radiation, the multilayer coating typically comprises a periodic or partly periodic sequence of layers made of a layer material with a low refractive index and a layer material with a high refractive index. The selection of the layer materials depends on the used wavelength, for which the multilayer coating should have maximum reflectivity. If the used wavelength lies at approximately 13.5 nm, the layers made of the material with a high refractive index are typically silicon and the layers made of the material with a low refractive index are typically molybdenum. Depending on the used wavelength, other material combinations such as e.g. molybdenum and beryllium, ruthenium and beryllium, or lanthanum and $B_4C$ are likewise possible.

In one development, the layer materials of the alternating layers of the multilayer coating and of the further multilayer coating are identical. This is advantageous since both the multilayer coating and the further multilayer coating may be applied in one and the same coating apparatus in this case. Cleaning of the surface of the further multilayer coating may also be carried out e.g. in situ in an EUV lithography apparatus in a common cleaning process with the multilayer coating.

In this case, the difference between the multilayer coating and the further multilayer coating merely consists in the different thickness of the layers and, optionally, in the different number of layers. Typically, at least one capping layer which is intended to protect the layers lying therebelow from oxidation or damage is applied to both the multilayer coating and the further multilayer coating. Intermediate layers which are intended to serve to prevent the diffusion between the layer materials with a high refractive index and the layer materials with a low refractive index are optionally present in both the multilayer coating and the further multilayer coating.

In one embodiment, the surface of the multilayer coating forms a contiguous first surface region of the mask, said first surface region covering 30% or more of the surface of the mask provided for imaging. In such a mask, at least 30% of the surface of the multilayer coating is exposed and may be imaged onto the first region of the light-sensitive layer in order to determine the DUV+EUV contrast or the dose to clear for the radiation reflected at the multilayer coating.

In a further embodiment, the surface of the further multilayer coating forms a contiguous second surface region of the mask, said second surface region covering more than 30% of the surface of the mask provided for imaging. In particular, the multilayer coating, the absorbing coating and the further coating may each cover approximately one third of the entire surface of the mask.

A further aspect of the invention relates to an EUV lithography apparatus comprising a mask embodied as described above. With the aid of the mask, it is possible to determine the contrast proportion caused by DUV radiation when imaging the mask onto a light-sensitive layer.

A further aspect of the invention relates to a method for determining a contrast proportion generated by DUV radiation when imaging a mask onto a light-sensitive layer, comprising: illuminating the mask with EUV radiation and DUV radiation for imaging the mask onto the light-sensitive layer, determining a radiation dose required for exposing a first region of the light-sensitive layer, wherein radiation which is reflected at a multilayer coating of the mask is incident on the light-sensitive layer in the first region, said multilayer coating being embodied both to reflect EUV radiation and to reflect DUV radiation, and determining a radiation dose required for exposing a second region of the light-sensitive layer, wherein radiation which is reflected by a further coating of the mask is incident on the light-sensitive layer in the second region, said further coating being embodied to suppress EUV radiation and to reflect DUV radiation, wherein the further coating is typically applied onto a coating which absorbs EUV radiation, and determining the contrast proportion by comparing the radiation doses required for exposing the first region and the second region.

As described further above in conjunction with the mask, the proportion of the overall contrast caused by DUV radiation may be determined by the comparison between the radiation dose required for exposing the first region and the radiation dose required for exposing the second region.

In a preferred variant, the contrast proportion $K_{DUV}/K_{DUV+EUV}$ is determined from the radiation dose $D_1$ required for exposing the first region and the radiation dose $D_2$ required for exposing the second region in accordance with the following formula described further above: $K_{DUV}/K_{DUV+EUV}=D_1/D_2$.

In one variant of the method, the wavelength-dependent reflectivity of the further coating, which is embodied as a multilayer coating, for DUV radiation in the wavelength range between 140 nm and 400 nm, preferably between 140 nm and 300 nm, is selected in such a way that it does not deviate by more than +/−5%, preferably by no more than +/−1%, from the wavelength-dependent reflectivity of the multilayer coating.

As presented further above, the wavelength-dependent reflectivity of the further multilayer coating for DUV radiation ideally corresponds to the wavelength-dependent reflectivity of the multilayer coating. In this way, the contrast proportion caused by DUV radiation may be determined with a high accuracy (see below).

In a further variant, the method additionally comprises: determining a radiation dose required for exposing a third region of the light-sensitive layer, wherein radiation which is reflected by a coating which absorbs EUV radiation is incident on the light-sensitive layer in the third region, and determining the contrast proportion taking into account the radiation dose required for exposing the third region. As indicated further above, the coating which absorbs EUV radiation does not necessarily also absorb radiation in the DUV range; rather, DUV radiation is typically also reflected at the absorbing coating. The radiation dose required for exposing the third region of the light-sensitive layer may be used to determine the contrast proportion caused by DUV radiation more precisely.

In one advantageous variant, the contrast proportion $K_{DUV}/K_{DUV+EUV}$ is determined from the radiation dose $D_1$ required for exposing the first region, the radiation dose $D_2$ required for exposing the second region and the radiation dose $D_3$ required for exposing the third region in accordance with the following formula: $K_{DUV}/K_{DUV+EUV}=(A_3/D_3+(A_1+A_2)/D_2)/(A_3/D_3+(A_1+A_2)/D_1)$, where $A_1$, $A_2$, $A_3$ denote the areas of the surfaces of the multilayer coating, the further coating and the coating which absorbs EUV radiation.

In order to determine the radiation dose required for exposure in each case, a plurality of exposures are typically carried out, in each case with a different time duration and hence with a different radiation dose. In so doing, all three regions of the light-sensitive layer may be exposed simultaneously; however, it is also possible to undertake the exposures of the three regions successively in time, with a light-sensitive layer with an identical composition (i.e. with an identical resist) being used for the exposure in each case. The illumination of the mask and the imaging of the mask onto the light-sensitive layer are typically carried out in the EUV lithography apparatus for which the contrast proportion generated by DUV radiation during the exposure of the light-sensitive layer or of the wafer is intended to be determined.

Further features and advantages of the invention emerge from the following description of exemplary embodiments of the invention, on the basis of the figures in the drawing, which show details essential to the invention, and from the claims. The individual features may be realized respectively on their own or together in any combination in one variant of the invention.

BRIEF DESCRIPTION OF THE DRAWINGS

Exemplary embodiments are illustrated in the schematic drawing and are explained in the following description. In the figures.

Identical reference signs are used in the following description of the drawings for components that are the same or functionally the same.

DETAILED DESCRIPTION

Figure 1:
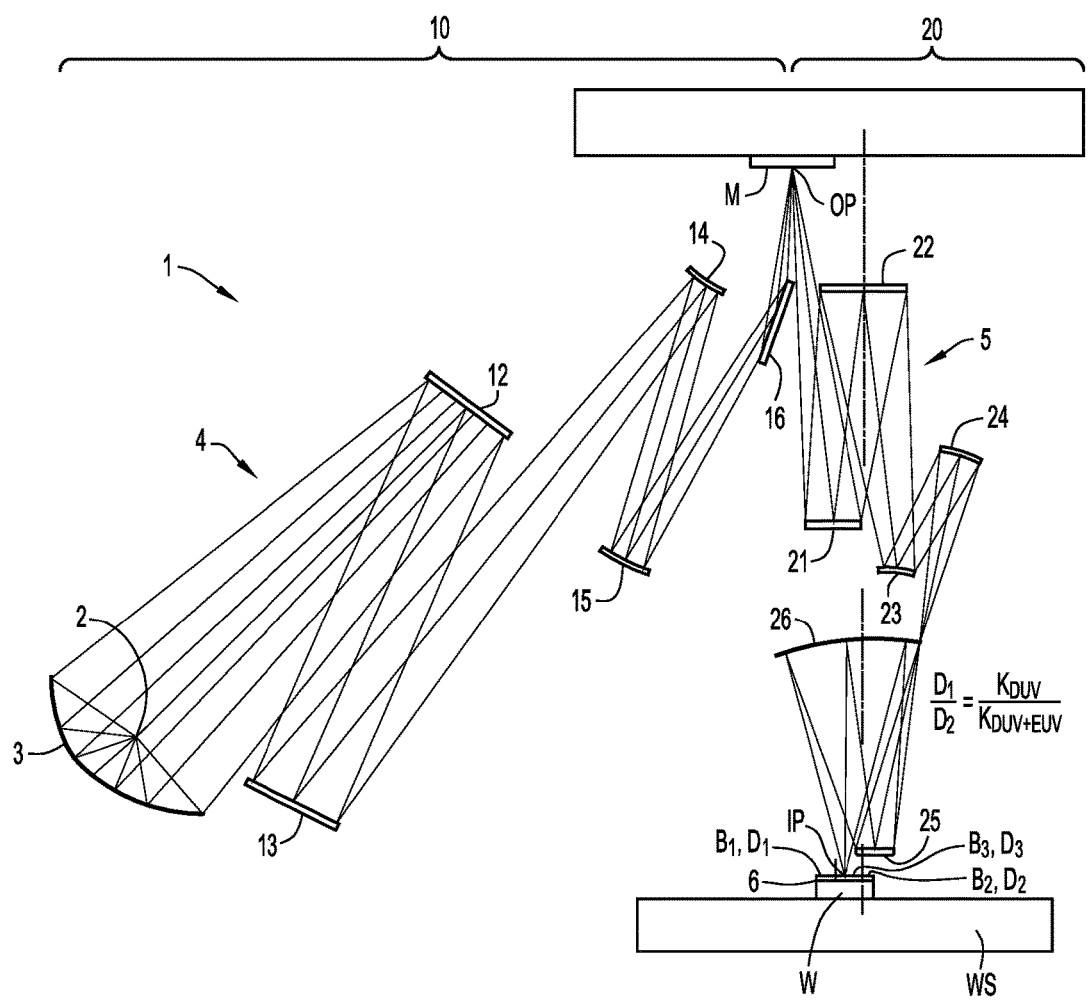
FIG. 1 shows a schematic illustration of an EUV lithography apparatus comprising an illumination system for illuminating a mask and comprising a projection system for imaging the mask onto a light-sensitive layer, FIG. 2A,B show schematic illustrations of a mask for the EUV lithography apparatus of FIG. 1 for the purposes of determining a contrast proportion caused by DUV radiation when exposing the light-sensitive layer, FIG. 3A,B show schematic illustrations of a mask analogous to FIG. 2A,B, which comprises a multilayer coating, an absorbing coating and a further multilayer coating, FIG. 4A,B show illustrations of the reflectivity of the multilayer coating and of the further multilayer coating of the mask of FIG. 3A,B in the EUV wavelength range.

FIG. 1 shows, very schematically, an optical arrangement in the form of an EUV lithography apparatus 1, which comprises an EUV light source 2 for generating EUV radiation having a high energy density in an EUV wavelength range between approximately 5 nm and approximately 20 nm. The EUV light source 2 may for example take the form of a plasma light source for generating a laser-induced plasma or be formed as a synchrotron radiation source. In the former case, in particular, a collector mirror 3 may be used, as shown in FIG. 1, in order to focus the EUV radiation of the EUV light source 2 into an illumination beam 4 and in this way increase the energy density further. The illumination beam 4 serves for the illumination of a reflective mask M using an illumination system 10, which comprises five reflecting optical elements 12 to 16 (mirrors) in the present example.

The wavelength spectrum emitted by the EUV light source 2 is not restricted to EUV radiation between approximately 5 nm and approximately 20 nm; rather, the EUV light source 2 also generates radiation at longer wavelengths, in particular in the DUV wavelength range between approximately 100 nm and approximately 400 nm and, possibly, radiation at even longer wavelengths in the VIS range or in the IR range.

The reflective mask M may comprise reflecting and non-reflecting or at least less strongly reflecting, or absorbing, regions, which form a structure to be imaged. In the shown example, a special mask M is used for the imaging, said mask being described in more detail below.

The mask M reflects part of the illumination beam 4 and forms a projection beam 5, which is radiated into a projection system 20, which generates an image of the mask M or of a respective portion thereof (see below) on a wafer W. The wafer W comprises a semiconductor material, for example silicon, and is arranged on a holder, which is also referred to as a wafer stage WS. A light-sensitive layer 6 (resist or photoresist), which is exposed by the projection beam 5, is applied onto the wafer W.

In the present example, the projection system 20 comprises six reflective optical elements 21 to 26 (mirrors) in order to generate an image of the mask M on the wafer W. The number of mirrors in a projection system 20 typically lies between four and eight; however, only two mirrors may also possibly be used.

In order to achieve a high imaging quality when imaging a respective object point OP of the mask M onto a respective image point IP on the wafer W or on the light-sensitive layer 6, highest requirements are to be imposed on the surface form of the mirrors 21 to 26; and the position or the alignment of the mirrors 21 to 26 in relation to one another and in relation to the mask M and the wafer W also requires precision in the nanometer range.

Figure 2A:
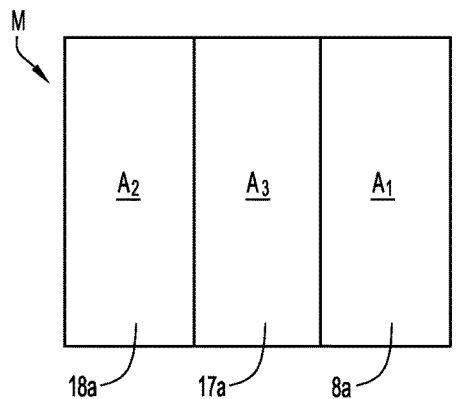
Figure 2B:
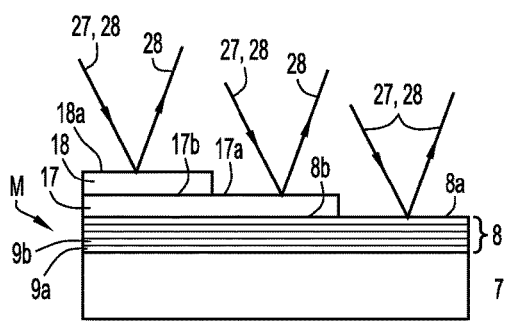
Figure 3B:
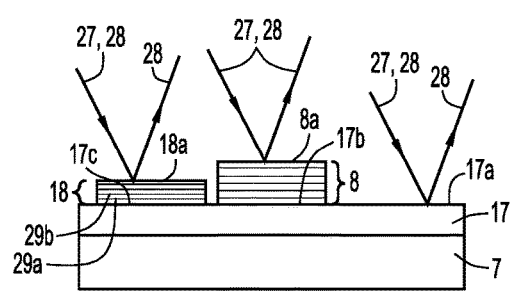

FIG. 2A,B show an example of a mask M for the EUV lithography apparatus 1 of FIG. 1, which comprises a substrate 7 made of a material with a low coefficient of thermal expansion, e.g. ULE®, Zerodur® or Clearceram®, in a plan view and in a section. The mask M typically has a rectangular basic form, with the sectional illustration shown in FIG. 2B being representative for the entire mask M; i.e., the structure of the mask M does not change in a direction perpendicular to the plane of the drawing.

A multilayer coating 8 comprising a plurality of alternating layers 9a, 9b made of a layer material with a high refractive index and a layer material with a low refractive index is applied to the substrate 7 of the mask M. The number of layers with a high refractive index and a low refractive index 9a, 9b depicted in FIG. 2 merely serves for illustrative purposes. Moreover, depicting a capping layer and depicting possibly present barrier layers for avoiding diffusion were dispensed with in the illustration of the multilayer coating 8 in FIG. 2B.

The typically periodic design of the reflective multilayer coating 8 (generally with pairs of layers 9a, 9b with an identical thickness) facilitates reflection of short-wavelength EUV radiation with a wavelength in the nm range (e.g. at a used wavelength $\lambda_B$ of 13.5 nm). As a rule, the layers 9a made of the material with a high refractive index are made of silicon and the layers 9b made of the material with a low refractive index are made of molybdenum in the case of a used wavelength $\lambda_B$ of 13.5 nm. Depending on the used wavelength in the EUV wavelength range, other material combinations such as e.g. molybdenum and beryllium, ruthenium and beryllium, or lanthanum and $B_4C$ are likewise possible.

The multilayer coating 8 comprises a surface 8a, at which the multilayer coating 8 is exposed, facing away from the substrate 7. The multilayer coating 8 comprises a portion 8b, onto which an absorbing coating 17 has been applied in the example shown in FIG. 2A,B. In the shown example, the absorbing coating 17 consists of a single layer having a metallic material, for example chromium, chromium oxide, titanium, titanium nitride, tantalum, tantalum nitride, etc. Where necessary, a barrier layer not depicted here may be applied between the absorbing coating 17 and the multilayer coating 8. In the mask M shown in FIG. 2A,B, the absorbing layer 17 has been applied onto the multilayer coating 8 over the entire area thereof, i.e. the absorbing coating 17 completely covers the portion 8b.

A further coating 18, which consists of a single layer of aluminum in the mask M shown in FIG. 2A,B, has been applied onto a portion 17b of the absorbing coating 17. Aluminum has a reflectivity of virtually 0% for incident EUV radiation 27 in a wavelength range between approximately 5 nm and approximately 20 nm while DUV radiation 28, i.e. radiation in a wavelength range between approximately 100 nm and approximately 400 nm, and consequently also between 140 nm and 400 nm or 300 nm, has a reflectivity of virtually 100%. Both the EUV radiation 27 incident on the mask M and the DUV radiation 28 incident on the mask M are part of the illumination beam 4 shown in FIG. 1.

As may be identified in FIG. 2a, the exposed surface 8a of the multilayer coating 8 forms a first surface region $A_1$ of the mask M, the exposed surface 18a of the further coating forms a second surface region $A_2$ of the mask M and the exposed surface 17a of the absorbing coating 17 forms a third surface region $A_3$ of the mask M.

Figure 3A:
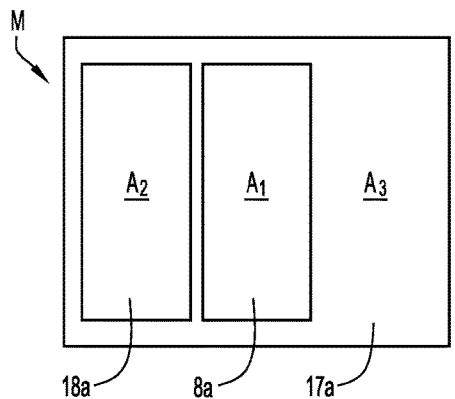

FIG. 3A,B show a further embodiment of the mask M which inter alia differs from the mask M depicted in FIG. 2 in that the further coating is embodied as a further multilayer coating 18. Moreover, the absorbing coating 17 is applied directly onto the substrate 7 and over the whole area thereof in the mask M depicted in FIGS. 3A,B. The multilayer coating 8 and the further multilayer coating 18 are applied onto the absorbing coating 17 at two different portions 17b, 17c and the surfaces 8a, 18a of said multilayer coating and further multilayer coating form a first surface region $A_1$ and a second surface region $A_2$ of the mask M, said surface regions being surrounded by a third surface region $A_3$ which is formed by the exposed surface 17a of the absorbing coating 17. It is understood that the mask M provided with the further multilayer coating 18 may alternatively have an embodiment as depicted in FIG. 2A,B.

The further multilayer coating 18 comprises a multiplicity of alternating layers 29a, 29b made of a layer material with a high refractive index and a layer material with a low refractive index, with the terms "high refractive index" and "low refractive index" relating to the refractive indices of the two layer materials 29a, 29b relative to one another, i.e. the layer material 29a with a high refractive index has a higher refractive index than the layer material 29b with a low refractive index.

In the shown example, the material of the layers 29a with a high refractive index is silicon and the material of the layers 29b with a low refractive index is molybdenum, i.e. the layer materials of the further multilayer coating 18 correspond to the layer materials of the multilayer coating 8. However, the layer thicknesses of the layers 9a, 9b of the multilayer coating 8 and the layer thicknesses of the layers 29a, 29b of the further multilayer coating 18 differ from one another, to be precise in such a way that the multilayer coating 8 has a maximum of the reflectivity R at a used wavelength $\lambda_B$ of approximately 13.5 nm while the further multilayer coating 18 has a reflectivity of less than 0.3% in a wavelength range of +/−0.5 nm around the used wavelength $\lambda_B$, as may be identified on the basis of the two reflectivity curves, depicted in FIG. 4A,B, for the reflectivity $R_1$ of the multilayer coating 8 and the reflectivity $R_2$ of the further multilayer coating 18.

Accordingly, the multilayer coating 8 is a coating which is highly reflective for EUV radiation 27 at the used wavelength $\lambda_B$ of approximately 13.5 nm, while the further multilayer coating 18 is embodied to suppress the reflection of EUV radiation 27 in a wavelength range lying around the used wavelength $\lambda_B$. The further multilayer coating 18, more precisely the layer thicknesses of the layer materials 29a, 29b, is/are selected in such a way that the further multilayer coating 18 reproduces the reflectivity R of the multilayer coating 8 in the DUV wavelength range, i.e. with wavelengths between 100 nm and 400 nm, preferably between 140 nm and 300 nm, as accurately as possible. This may likewise be achieved by virtue of the layer thicknesses of the layers 29a, 29b and the number of layers of the further multilayer coating 18 being selected in a suitable manner, with the optimization typically being carried out with the aid of numerical calculations.

Figure 5:
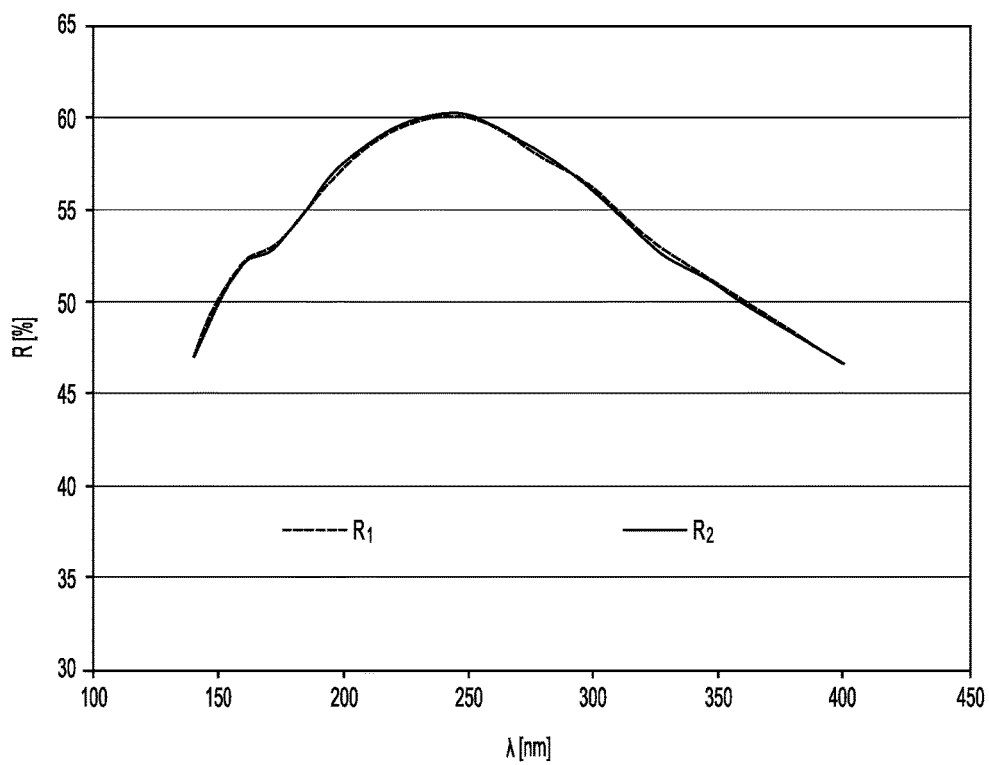
FIG. 5 shows an illustration of the reflectivity of the multilayer coating and of the further multilayer coating of the mask of FIG. 3A,B in the DUV wavelength range.

FIG. 5 shows the reflectivity $R_1$ of the multilayer coating 8 and the reflectivity $R_2$ of the further multilayer coating 18 in the wavelength range between approximately 140 nm and approximately 400 nm. Practically no difference can be identified in FIG. 5 between the reflectivity $R_1$ of the multilayer coating 8 and the reflectivity $R_2$ of the further multilayer coating 18 in this wavelength range. In general, what may be achieved by the optimization is that the wavelength-dependent reflectivity $R_2$ of the further multilayer coating 18 for DUV radiation 28 in the wavelength range between 140 nm and 400 nm does not deviate by more than +/−5%, preferably by no more than +/−1%, from the wavelength-dependent reflectivity R of the multilayer coating 8.

Figure 4A:
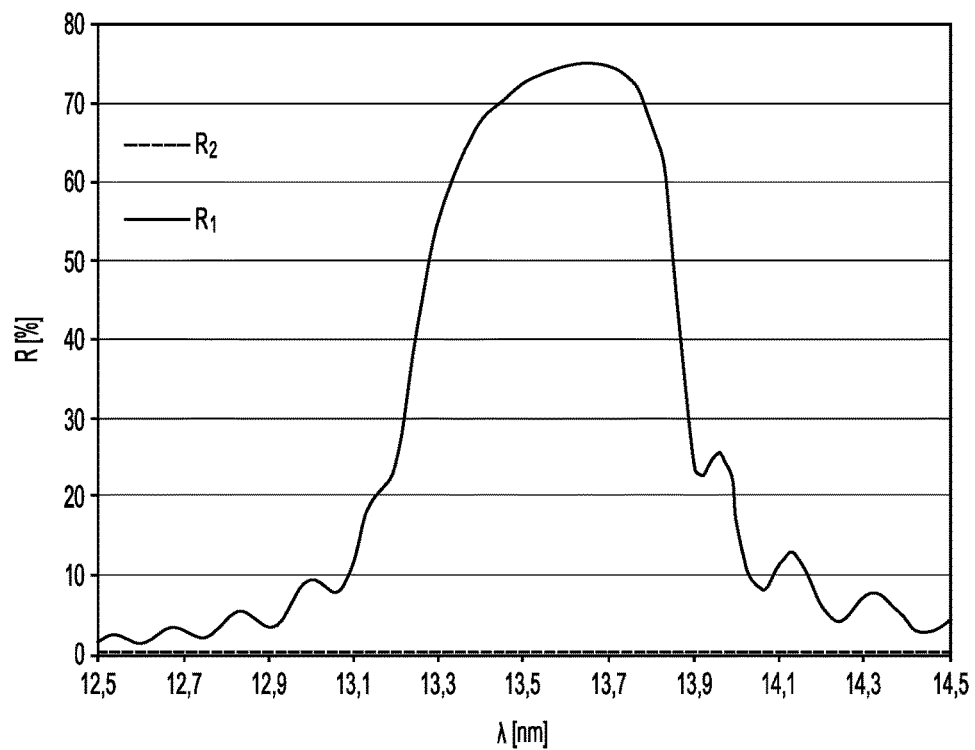
Figure 4B:
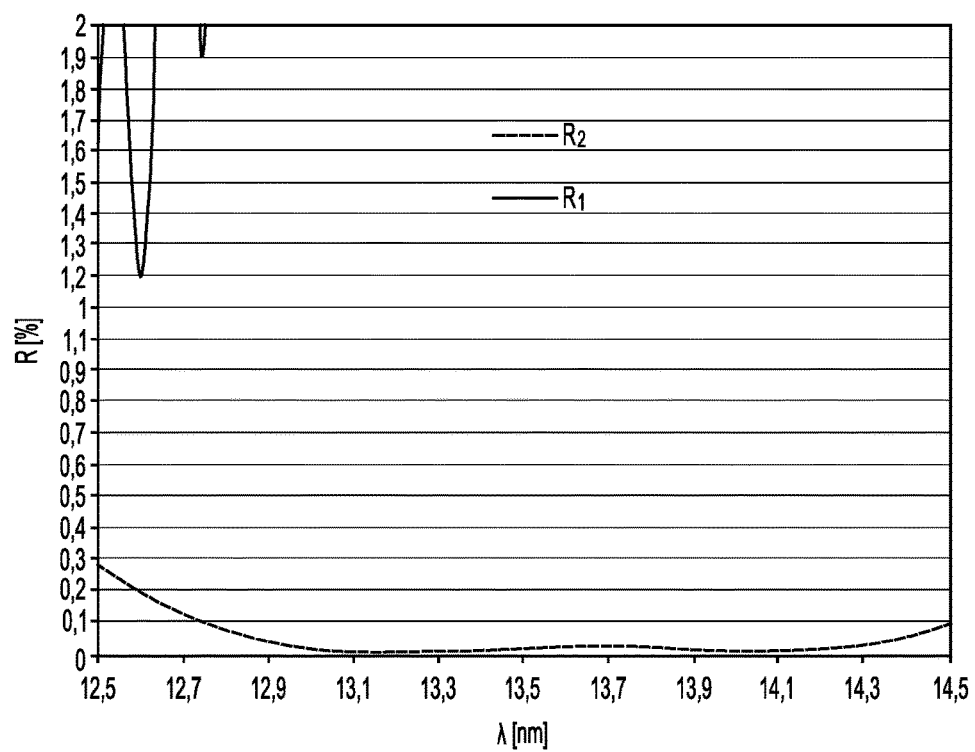

A layer design for the further multilayer coating, which generates the wavelength-dependent reflectivity $R_1$ or $R_2$, shown in FIG. 4A,B and FIG. 5, is described below. The following periodic design was used for the multilayer coating 8: Vacuum/60×(3 nm Mo/4 nm a-Si)/substrate. The aperiodic design of the further multilayer coating 18 may be gathered from the following table:

TABLE 1

| Layer thickness (nm) | Material |
| --- | --- |
|  | Vacuum |
| 0.695 | Mo |
| 7.74 | a-Si |
| 7.896 | Mo |
| 2.083 | a-Si |
| 0.663 | Mo |
| 4.216 | a-Si |
| 14.972 | Mo |
|  | Absorber |
|  | Substrate |

The masks M shown in FIG. 2A,B and FIG. 3A,B serve to determine a contrast proportion $K_{DUV}/K_{DUV+EUV}$ caused by the DUV radiation 28 when imaging the mask M onto the light-sensitive layer 6 in the EUV lithography apparatus 1 of FIG. 1 using a method described below.

For exposure or imaging purposes, the mask M of FIGS. 3a,b is positioned in the EUV lithography apparatus 1 and the light source 2 is activated such that the illumination beam 4, which contains both EUV radiation 27 and DUV radiation 28, is incident on the mask M. During the imaging, the first surface region $A_1$ with the multilayer coating 8 is imaged onto a first region $B_1$ of the light-sensitive layer 6 (cf. FIG. 1), the second surface region $A_2$ with the further multilayer coating 18 is imaged onto a second region $B_2$ of the light-sensitive layer 6 and the third surface region 17a, in which the absorbing coating 17 is exposed, is imaged onto a third region $B_3$ of the light-sensitive layer 6.

Hence, EUV radiation 27 and DUV radiation 28, which was reflected at the multilayer coating 8, are incident on the first region $B_1$, while only DUV radiation 28 is incident on the second region $B_2$ since the further multilayer coating 18 is embodied to suppress the reflection of EUV radiation 27. The EUV light source 2 is switched off after a predetermined period of time. The procedure described above is repeated with an increasing length of time during which the EUV light source 2 is activated until a first radiation dose $D_1$ ("dose to clear"), at which the light-sensitive layer 6 has been exposed through in the first region $B_1$, and a second radiation dose $D_2$, at which the light-sensitive layer 6 has been exposed through in the second region $B_2$, may be determined.

In order to check whether the radiation dose $D_1$, $D_2$ has been achieved, the light-sensitive layer 6 or the wafer W is removed from the EUV lithography apparatus 1 and developed using a photochemical method. Typically, a number of exposures with different time durations are undertaken on adjacent surface regions of the same light-sensitive layer 6; i.e., it is not necessary to replace the light-sensitive layer 6 after each exposure.

The radiation dose $D_1$ required for exposing the first region $B_1$ is less than the radiation dose $D_2$ required for exposing the second region $B_2$ since both EUV radiation 27 and DUV radiation 28 are incident in the first region $B_1$, i.e. $D_1 < D_2$ applies. The contrast ratio $K_{DUV}/K_{DUV+EUV}$ corresponds to the ratio of the two radiation doses D1, D2, i.e. the following applies:

$$D_1/D_2 = K_{DUV}/K_{DUV+EUV}.$$

Additionally, a third radiation dose $D_3$ may also be determined in the mask M shown in FIG. 2A,B and FIG. 3A,B, said third radiation dose being required for exposing the third region $B_3$ of the light-sensitive layer 6. Radiation, in particular DUV radiation 28, which is reflected by the coating 17 which absorbs EUV radiation 27 is incident on the light-sensitive layer 6 in the third region $B_3$, provided said absorbing coating does not facilitate a sufficient suppression of the reflection of radiation in this wavelength range. Since the masks employed for producing semiconductors in the EUV lithography apparatus 1 have a structured absorbing coating 17, in which coated regions of the multilayer coating 8 alternate with uncoated regions, the determination of the DUV contrast proportion may be refined by measuring the third radiation dose $D_3$ required for exposing the third region $B_3$ if the surface area $A_3$ of the absorbing coating 17 is known or if the proportion of the absorbing coating 17 of the entire surface $A_1+A_2+A_3$ of the mask M to be imaged is known.

In this case, the following formula may be used for determining the contrast proportion $K_{DUV}/K_{DUV+EUV}$:

$$K_{DUV}/K_{DUV+EUV} = (A_3/D_3 + (A_1+A_2)/D_2)/(A_3/D_3 + (A_1+A_2)/D_1),$$

where $A_1$, $A_2$, $A_3$ denote areas of the surfaces 8a, 18a, 17a of the multilayer coating 8, the further coating 18 and the coating 17 which absorbs EUV radiation 27.

In order to simplify the determination of the radiation doses $D_1$, $D_2$, $D_3$, it is advantageous if the absorbing coating 17 forms a contiguous surface region $A_3$ of no more than approximately 30-40% of the entire surface $A_1+A_2+A_3$ of the mask M, as is the case in the masks M shown in FIG. 2A,B and FIG. 3A,B. It is likewise advantageous if the multilayer coating 8 and the further multilayer coating 18 each form a contiguous surface region $A_1$, $A_2$, which respectively covers 30% or more of the entire surface $A_1+A_2+A_3$ of the mask M. What this may achieve is that the first region $B_1$, the second region $B_2$ and the third region $B_3$ of the light-sensitive layer 6 have approximately the same size, i.e. each one of the three regions $B_1$ to $B_3$ provides approximately a third of the exposed area of the light-sensitive layer 6 in each case.

In the manner described further above, it is possible to precisely determine the contrast proportion of the DUV radiation 28 which, in addition to the EUV radiation 27, contributes to the exposure of the light-sensitive layer 6. Typically, the light-sensitive layer 6 is not sensitive to radiation at longer wavelengths, i.e. in the VIS or IR wavelength range, and so radiation at these wavelengths does not contribute, or only contributes to a negligible proportion, to the contrast.

What is claimed is:

1. A mask for extreme ultraviolet (EUV) lithography, comprising:
   a substrate having:
   a first surface region ($A_1$) formed by a surface of a multilayer coating embodied to reflect EUV radiation, said multilayer coating surface facing away from the substrate, and
   a second surface region ($A_2$) formed by a surface of a further coating embodied to reflect deep ultraviolet (DUV) radiation and to suppress the reflection of the EUV radiation, said further coating surface facing away from the substrate, wherein the further coating is a further multilayer coating,
   wherein the wavelength-dependent reflectivity of the further multilayer coating for the DUV radiation in the wavelength range between 140 nm and 400 nm does not deviate by more than +/−5% from the wavelength-dependent reflectivity of the multilayer coating.

2. The mask as claimed in claim 1, further comprising: a third surface region ($A_3$) formed by a surface of a coating absorbing the EUV radiation, said EUV radiation absorbing surface facing away from the substrate.

3. The mask as claimed in claim 1, wherein the reflectivity of the further coating is less than 0.3% at a used wavelength ($\lambda_B$) of the EUV radiation at which the reflectivity of the multilayer coating is at a maximum.

4. The mask as claimed in claim 1, wherein the multilayer coating comprises a plurality of alternating layers made respectively of a layer material with a high refractive index and a layer material with a low refractive index.

5. The mask as claimed in claim 4, wherein the layer materials of the alternating layers of the multilayer coating and of the further multilayer coating are identical.

6. The mask as claimed in claim 1, wherein the surface of the multilayer coating forms a contiguous first surface region ($A_1$) of the mask, said first surface region covering 30% or more of the surface ($A_1+A_2+A_3$) of the mask provided for imaging.

7. The mask as claimed in claim 1, wherein the surface of the further multilayer coating forms a contiguous second surface region ($A_2$) of the mask, said second surface region covering 30% or more of the surface ($A_1+A_2+A_3$) of the mask provided for imaging.

8. The mask as claimed in claim 1, wherein the wavelength-dependent reflectivity of the further multilayer coating for the DUV radiation in the wavelength range between 140 nm and 400 nm does not deviate by more than +/−1% from the wavelength-dependent reflectivity of the multilayer coating.

9. The mask as claimed in claim 3, wherein the reflectivity of the further coating is less than 0.1%, at a used wavelength ($\lambda_B$) of the EUV radiation at which the reflectivity of the multilayer coating is at a maximum.

10. An EUV lithography apparatus comprising: a mask as claimed in claim 1.

11. A method for determining a contrast proportion ($K_{DUV}/K_{DUV+EUV}$) caused by DUV radiation when imaging a mask onto a light-sensitive layer, comprising:
    illuminating the mask with radiation for imaging the mask onto the light-sensitive layer,
    determining a radiation dose ($D_1$) required for exposing a first region ($B_1$) of the light-sensitive layer, wherein radiation which is reflected at a multilayer coating of the mask is incident on the light-sensitive layer in the first region, said multilayer coating being embodied both to reflect EUV radiation and to reflect DUV radiation, and
    determining a radiation dose ($D_2$) required for exposing a second region ($B_2$) of the light-sensitive layer, wherein radiation which is reflected by a further coating of the mask is incident on the light-sensitive layer in the second region ($B_2$), said further coating being embodied to suppress EUV radiation and to reflect DUV radiation, and
    determining the contrast proportion ($K_{DUV}/K_{DUV+EUV}$) by comparing the radiation doses ($D_1$, $D_2$) required for exposing the first region ($B_1$) and for exposing the second region ($B_2$),
    wherein the wavelength-dependent reflectivity of the further coating, which is embodied as a multilayer coating, for DUV radiation in the wavelength range between 140 nm and 400 nm is selected to not deviate by more than +/−5% from the wavelength-dependent reflectivity of the multilayer coating.

12. The method as claimed in claim 11, wherein the contrast proportion $K_{DUV}/K_{DUV+EUV}$ is determined from the radiation dose $D_1$ required for exposing the first region ($B_1$) and the radiation dose $D_2$ required for exposing the second region ($B_2$) in accordance with the following formula:

$$K_{DUV}/K_{DUV+EUV}=D_1/D_2.$$

13. The method as claimed in claim 11, further comprising: determining a radiation dose ($D_3$) required for exposing a third region ($B_3$) of the light-sensitive layer, wherein radiation which is reflected by a coating which absorbs EUV radiation is incident on the light-sensitive layer in the third region ($B_3$), and determining the contrast proportion ($K_{DUV}/K_{DUV+EUV}$) taking into account the radiation dose ($D_3$) required for exposing the third region ($B_3$).

14. The method as claimed in claim 13, wherein the contrast proportion $K_{DUV}/K_{DUV+EUV}$ is determined from the radiation dose $D_1$ required for exposing the first region ($B_1$), the radiation dose $D_2$ required for exposing the second region ($B_2$) and the radiation dose $D_3$ required for exposing the third region ($B_3$) in accordance with the following formula:

$$K_{DUV}/K_{DUV+EUV}=(A_3/D_3+(A_1+A_2)/D_2)/(A_3/D_3+(A_1+A_2)/D_1),$$

where $A_1$, $A_2$, $A_3$ denote areas of the surfaces of the multilayer coating, the further coating and the coating which absorbs EUV radiation.

15. The method as claimed in claim 11, wherein the further coating is embodied as a multilayer coating.

16. The method as claimed in claim 11, wherein the wavelength-dependent reflectivity of the further coating, which is embodied as a multilayer coating, for DUV radiation in the wavelength range between 140 nm and 400 nm is selected to not deviate by more than +/−1% from the wavelength-dependent reflectivity of the multilayer coating.

* * * * *

UNITED STATES PATENT AND TRADEMARK OFFICE
CERTIFICATE OF CORRECTION

PATENT NO. : 10,156,782 B2
APPLICATION NO. : 15/431306
DATED : December 18, 2018
INVENTOR(S) : Huber Page 1 of 2

It is certified that error appears in the above-identified patent and that said Letters Patent is hereby corrected as shown below:

In the Specification

Column 8, Line 5, Delete "FIG." and insert -- FIGS. --, therefor.

Column 8, Line 9, Delete "FIG." and insert -- FIGS. --, therefor.

Column 8, Line 10, Delete "FIG." and insert -- FIGS. --, therefor.

Column 8, Line 12, Delete "FIG." and insert -- FIGS. --, therefor.

Column 8, Line 14, Delete "FIG." and insert -- FIGS. --, therefor.

Column 8, Line 17, Delete "FIG." and insert -- FIGS. --, therefor.

Column 9, Line 9, Delete "FIG." and insert -- FIGS. --, therefor.

Column 9, Line 45, Delete "FIG." and insert -- FIGS. --, therefor.

Column 9, Line 51, Delete "FIG." and insert -- FIGS. --, therefor.

Column 9, Line 56, Delete "FIG." and insert -- FIGS. --, therefor.

Column 10, Line 7, Delete "FIG." and insert -- FIGS. --, therefor.

Column 10, Line 22, Delete "FIG." and insert -- FIGS. --, therefor.

Column 10, Line 46, Delete "FIG." and insert -- FIGS. --, therefor.

Column 10, Line 55, Delete "29a ," and insert -- 29a, --, therefor.

Signed and Sealed this
Fourth Day of February, 2020

Andrei Iancu
*Director of the United States Patent and Trademark Office*

CERTIFICATE OF CORRECTION (continued)
U.S. Pat. No. 10,156,782 B2

Column 11, Line 15, Delete "FIG." and insert -- FIGS. --, therefor.

Column 11, Line 34, Delete "FIG." (both occurrences) and insert -- FIGS. --, therefor.

Column 12, Line 17, Delete "FIG." (both occurrences) and insert -- FIGS. --, therefor.

Column 12, Line 48, Delete "FIG." and insert -- FIGS. --, therefor.

Column 12, Line 49, Delete "FIG." and insert -- FIGS. --, therefor.